United States Patent [19]

Hay

[11] Patent Number: 5,001,294

[45] Date of Patent: Mar. 19, 1991

[54] SYNTHESIS OF DIARYL ALKENES

[76] Inventor: Allan S. Hay, 5015 Glencairn Ave., Montreal, Quebec, Canada, H3W 2B3

[21] Appl. No.: 267,111

[22] Filed: Oct. 31, 1988

[51] Int. Cl.$^5$ .......................... C07C 1/253; C07C 1/20
[52] U.S. Cl. ..................................... 585/436; 585/469; 544/180; 544/242; 546/181; 546/352; 548/202; 548/131; 548/152; 548/511; 549/80; 568/592; 568/631
[58] Field of Search ............... 585/436, 469; 568/592, 568/631, 57; 544/180, 242; 546/352, 181; 548/152, 133, 131, 217, 202, 235, 247, 250, 255, 335, 373, 511; 549/80

[56] References Cited

U.S. PATENT DOCUMENTS

| 3,819,615 | 6/1974 | Siegrist | 585/436 |
| 3,879,463 | 4/1975 | Peters, Jr. et al. | 568/631 |
| 3,904,678 | 9/1975 | Scheuermann et al. | 568/631 |
| 3,991,049 | 11/1976 | Siegrist et al. | 568/631 |
| 4,158,099 | 6/1979 | Siegrist et al. | 568/636 |
| 4,335,055 | 6/1982 | Blaser | 568/631 |

Primary Examiner—H. M. S. Sneed
Assistant Examiner—J. Saba
Attorney, Agent, or Firm—Swabey Ogilvy Renault

[57] ABSTRACT

Aromatic alkenes, especially diarylbutadienes are produced in a simple economic process by reaction of an anil with an organic compound having a non-aromatic unsaturated system conjugated with an aromatic system, and a terminal methyl group pendent from the non-aromatic unsaturated system; in particular the organic compound is a propenyl-substituted aromatic compound.

10 Claims, No Drawings

SYNTHESIS OF DIARYL ALKENES

BACKGROUND OF THE INVENTION (i) Field of the Invention

This invention relates to a process for preparing aromatic alkenes, especially butadienes, and novel bis-dienes.

(ii) Description of Prior Art

The most common method used in the past for the synthesis of diarylbutadienes involves the Wittig reaction using phosphonium salts (cf R. N. McDonald & T. W. Campbell, J. Org. Chem., 24, 1969 (1959)).

Two methods for the synthesis are outlined below. The reactions proceed in high yield but require the use of molar amounts of the expensive triphenylphosphine in the reaction which is converted to triphenylphosphine oxide. It also requires the synthesis of benzyl or phenylpropenyl halides as intermediates.

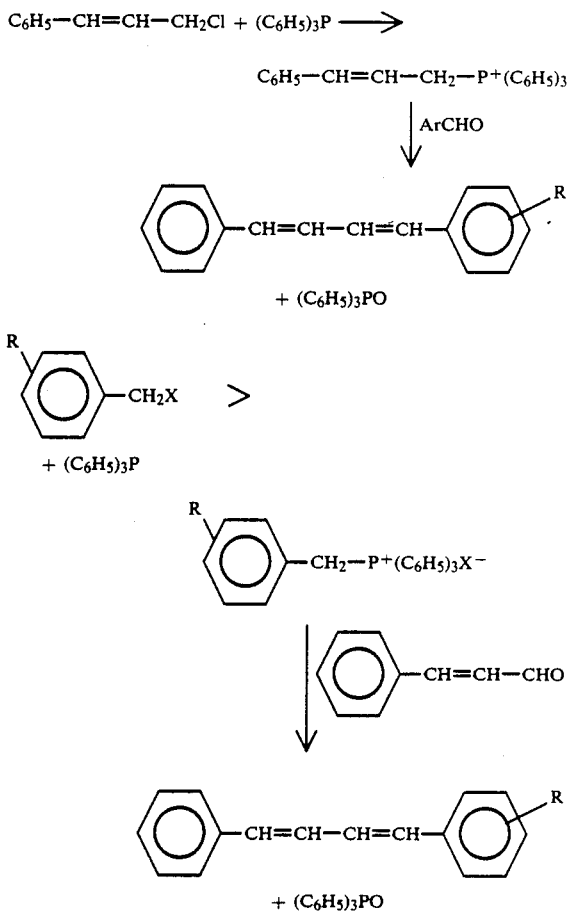

In a series of papers and patents Siegrist (A. E. Siegrist, Helv. Chim. Acta, 50, 906 (1960), et seq; A. E. Siegrist, P. Liechti, H. R. Meyer and K. Weber U.S. Pat. No. 4,158,099, June 12, 1979) demonstrated a facile synthesis of stilbenes by the condensation of anils of aromatic aldehydes, which are readily accessible from the condensation of the aldehydes with aniline, with methyl-substituted aromatic compounds.

Siegrist prepared several thousand stilbenes from heterocyclic compounds as well as hydrocarbons and in many cases yields of over 90 percent were obtained. The reaction proceeds under relatively mild conditions in aprotic dipolar solvents such as N,N'-dimethylformamide with bases such as potassium hydroxide or potassium t-butoxide because the coproduct in the reaction is aniline and hence the high basicity of the reaction mixture can be maintained.

An attempt has been made to synthesize polymeric stilbenes using the anil reaction (G. Kofsmehl and A. Yarridjanian, Makromol. Chem. 182, 3419 (1981)). The polymers were not thoroughly characterized, however it is unlikely that high molecular weight materials were formed since the reaction is not a high yield reaction and the insoluble polymers when formed would precipitate from the reaction mixture before high molecular weight could be obtained. The synthesis of bifunctional monomers or oligomers containing stilbene moieties by this method is possible. For example, one could synthesize either a dihydroxystilbene or a stilbene dicarboxylic acid by this route and these materials could be used in the synthesis of thermotropic aromatic polyesters which could subsequently be crosslinked with molecules such as maleic anhydride as in the recent work described by Calundann et al (cf. G. W. Calundann, H. A. A. Rasoul and H. K. Hall, Jr., U.S. Pat. No. 4,654,412 (Mar. 31, 1987)).

SUMMARY OF THE INVENTION

It is an object of this invention to provide a novel process for the synthesis of aromatic dienes, especially butadienes, including diaryl, dihetaryl and arylhetaryl butadienes.

It is a further object of this invention to provide such a process for the synthesis of such aromatic dienes which is susceptible to wide variations in the nature of the aromatic moieties.

It is a still further object of this invention to provide novel aromatic bis-dienes.

In accordance with this invention there is provided a process for preparing an alkene in which an anil is reacted with an organic compound having a non-aromatic unsaturated system conjugated with an aromatic system and a terminal methyl group pendent from said non-aromatic unsaturated system.

DESCRIPTION OF PREFERRED EMBODIMENTS

The alkenes produced by the process of the invention may be represented by the formula (I):

$$R_1-CH=CH-X-R_2 \qquad (I)$$

wherein $R_1$ and $R_2$, which may be the same or different, are selected from aryl and hetaryl radicals, and X is a divalent unsaturated radical having unsaturation conjugated with the unsaturation of $R_2$.

Suitable aryl radicals include mono-, bi-, tri- and tetracyclic hydrocarbon aromatic radicals, for example naphthalenes, anthracenes, phenanthrenes, pyrenes, biphenyls, terphenyls, especially phenyl.

The hetaryl radicals are to be understood as heteroaromatic radicals, for example pyridines, pyrimidines, triazines, furans, benzofurans, naphthofurans, dibenzofurans, oxazoles,, isoxazoles, oxadiazoles; benzoxazoles, naphthoxazoles! benzisoxazoles, thiophenes, dibenzothiophenes, thiazoles, benzothiazoles, indoles, pyrazoles, imidazoles, benzimidazoles, triazoles, quinolines and quinoxalines.

The aryl and hetaryl radicals may be unsubstituted or substituted.

The anils employed in the process of the invention may be represented by the formula (II):

$$R_1-CH=NR_3 \qquad (II)$$

wherein $R_1$ is as defined above and $R_3$ is an aryl radical, especially phenyl.

Optional substituents in the aryl or hetaryl radical $R_1$ include lower alkyl, lower alkoxy and halo.

The organic compound having a terminal methyl group pendent the conjugated system may be represented by formula (III):

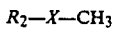

$$R_2-X-CH_3 \qquad (III)$$

in which $R_2$ and X are as defined above.

In particular X is a divalent olefinic radical and in particular an ethylene radical whereby $-X-CH_3$ in formula (III) is propenyl and the alkenes (I) are butadienes.

Suitable substituents in the aryl or hetaryl radical $R_2$ are for example cyano; arylsulfone; fluorine, chlorine, bromine, iodine; aryl, hetaryl; t-alkyl, dialkylaryl, alkyldiaryl; styryl, phenylethynyl, alkoxy, aryloxy, thioalkoxy, thioaryloxy; dialkylamino, alkylarylamino and diarylamino; preferred substituents are the electron-withdrawing groups for example cyano, arylsulfone and halogens since these increase the acidity of the protons on the pendent terminal methyl.

The substituents may also be lower alkyl however methyl groups will also react with the anil thus competing with the terminal pendent methyl, particularly producing mixed stilbene/butadiene systems.

The anil starting compounds are readily prepared by condensation of aromatic aldehydes with aniline.

The reaction is suitably carried out in a basic medium. It has been found to be especially advantageous to employ strong bases for example alkali metal amides in inert solvents. In this regard it has been found to be particularly advantageous to employ sodium in dimethylformamide, whereby sodium amide is formed in situ and the dimethylformamide also functions as a solvent for the reaction. Using a strong base the reaction proceeds rapidly at 60° C. to 120° C., preferably 80° C. to 110° C.

If electron-withdrawing substituents are present on $R_2$, weaker bases and lower temperatures may be employed.

Generally speaking it is appropriate to carry out the reaction in a strongly basic alkali compound with an N-dialkyl-acylamide as solvent. Suitable alkali compounds include potassium hydroxide, potassium t-butylate, sodium methylate, sodium hydroxide, sodium amide, lithium amide, lithium hydroxide, rubidium hydroxide and cesium hydroxide.

The reactants are preferably reacted in equivalent quantities so that neither is present in a significant excess.

Some aromatic butadienes, in particular diphenylbutadienes, are already known and are readily polymerized by anionic or radical polymerization techniques to produce high molecular weight polymers; they are also readily copolymerized with vinyl monomers.

The process of the present invention provides a route for readily obtaining a wide range of aromatic alkenes, especially butadienes, thereby making possible the economic production of a wide range of polymers and copolymers.

Among the aromatic alkenes produced by the process of the invention is a novel class of bis-alkenes derived from dianils of formula (X):

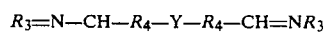

$$R_3=N-CH-R_4-Y-R_4-CH=NR_3 \qquad (X)$$

wherein $R_4$ is an arylene or hetarylene radical derived from the same class as for $R_1$, Y is a divalent bridging group and $R_3$ is as defined above.

Suitable bridging groups Y include alkylene, arylene, heteroarylene, $-OZO-$ and $-SZS-$ wherein Z is alkylene, arylene or heteroarylene. The bridging group Y may be o, m or on $R_4$ relative to the $R_3=N-CH-$ radical.

The resulting novel aromatic bis-alkenes which constitute a further aspect of the invention may be represented by formula (XI):

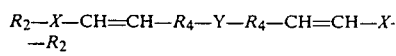

$$R_2-X-CH=CH-R_4-Y-R_4-CH=CH-X-\\-R_2 \qquad (XI)$$

wherein $R_2$, $R_4$, X and Y are as defined above.

The aromatic alkenes (I) and bis-alkenes (XI) and especially the butadienes and bis-butadienes may be employed to produce a wide range of polymers and copolymers.

The aromatic butadienes (I) will react with maleic anhydride in a Diels-Alder reaction to yield, after dehydrogenation of the intermediate tetrahydro compound, an aromatic phthalic anhydride (IV) (K. Alder and M. Schumacher Ann. 571, 87 (1951)).

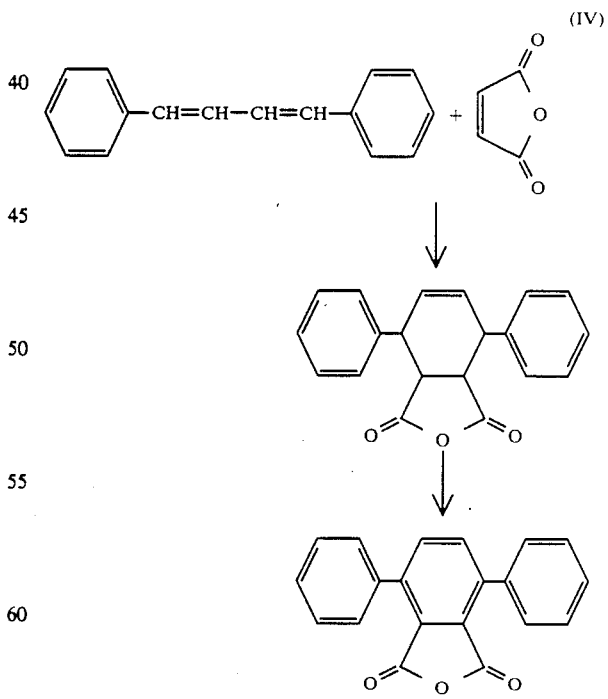

By extending the synthesis to the reaction of dimethyl-substituted aromatics (e.g. $CH_3.CH=CHArCH=CH.CH_3$), one could obtain aromatic dianhydrides (V):

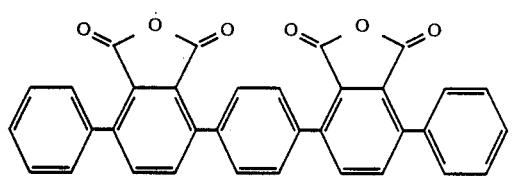 (V)

By reacting these dianhydrides (V) with diamines such as p-phenylenediamine, aromatic polyimides (VI) would be formed:

(VI)

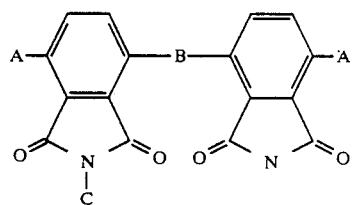 (VII)

Thus in accordance with the invention polymers can be designed to demonstrate the wide variation possible in glass temperatures, solvent resistance and thermo-oxidative stability.

A large number of other reactions of diarylbutadienes have appeared in the prior art, some of which are outlines below. The reaction of a bisdiene with benzoquinone, naphthoquinone, etc., for example, might also be the basis for a synthesis of polymeric anthraquinones or polymer intermediates. The polymers would be expected to be vary stable thermally and oxidatively as well as being redox polymers.

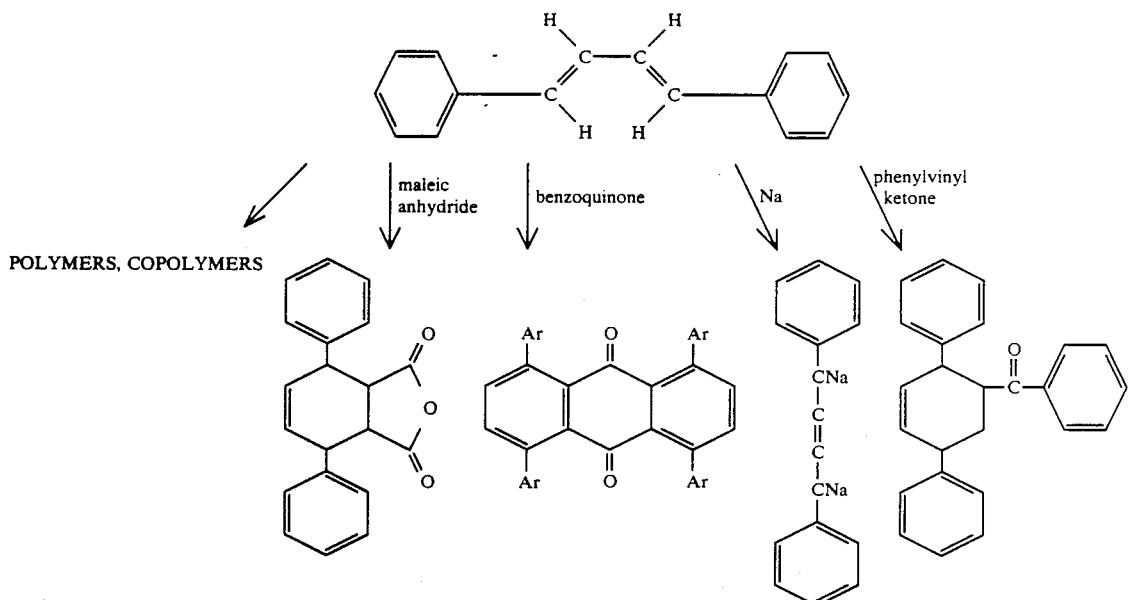

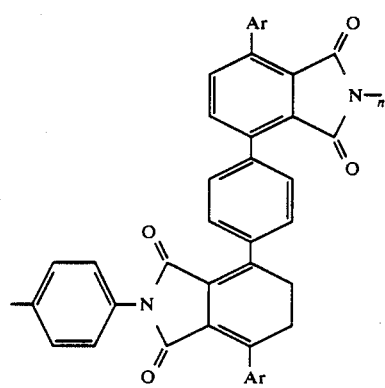

A wide variation in properties of the polyimides can potentially be obtained by varying the substituents in the initial aldehyde (A), aromatic hydrocarbon (B) or the diamine (C) as illustrated by reference to formula (VII):

Thus in accordance with the present invention anils have successfully been reacted with various propenylbenzene derivatives; thus, by way of example:

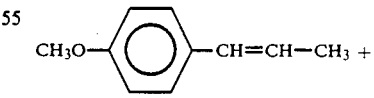

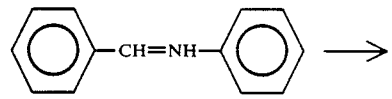

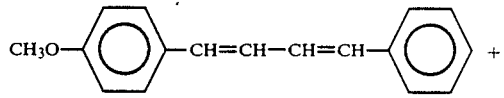

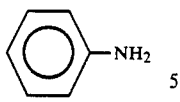

The reaction of anethole with benzaldehyde anil gives 4-methoxydiphenylbutadiene as product. Starting with p-hydroxybenzaldehyde the anil of the formal derivative was synthesized which on reaction with anethole gives a bisdiphenylbutadiene as product.

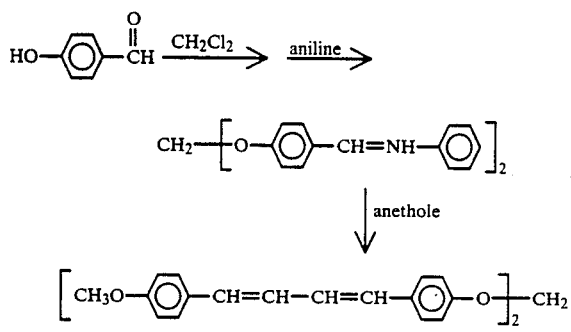

Potentially the simplest route to a bis-diene involves 4-propenylphenol as an intermediate since it would be readily available by the following route:

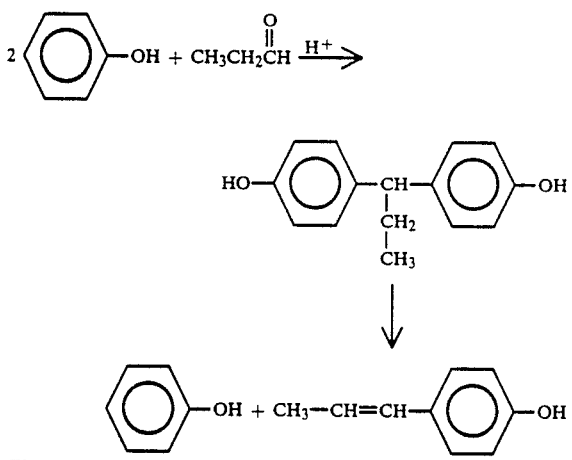

The 4-propenylphenol could be reacted via nucleophilic substitution to yield a large variety of bispropenyl compounds (VIII) having aliphatic or aromatic bridges $R_4$:

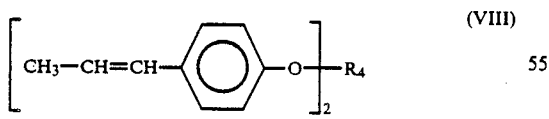

(VIII)

EXPERIMENTAL

General Procedure for the Preparation of the Sodium/dimethylformamide (Na/DMF) Mixture To dimethylformamide, 40 to 50 ml, was added sodium (1.0 g., 0.043 mol) in 7 portions at 105°–110° C. under a slow stream of nitrogen and with stirring. Additional portions of sodium were introduced after the initial vigorous reaction had abated. The mixture was brought to the desired temperature and the substrates were added using the remaining volume of dimethylformamide to dissolve them.

SYNTHESIS OF ANILS

N-phenylbenzaldimine

Benzaldehyde (31.84 g, 0.300 mol) and aniline (27.94 g, 0.300 mol) in benzene (100 ml) were heated to remove the water using a Dean-Stark trap. After 5.4 ml of water had been collected, the benzene was stripped off and the residual oil poured into a beaker. On treating with petroleum ether (10–20 ml) the oil crystallized. This mass was filtered under suction and washed with some additional petroleum ether. Recrystallization from hexanes gave off-white needles.

4-Methoxy-N-phenylbenzaldimine

The preparation follows that above with 4-methoxybenzaldehyde instead of benzaldehyde. Recrystallization from petroleum ether 30°–60° C. gave prisms mp 64°–65° C.

General Procedure for the Reaction of Anils with 1-arylpropenes

The methyl aromatic compound (or 1-arylpropene), 0.010 mol (i.e. 0.010 mol of methyl groups), and the Schiff base, 0.010 mol (or 0.010 mol of imine groups), were dissolved in dimethylformamide, 10 ml, and introduced into the stirred Na/DMF mixture, described above, at the stated temperature under a slow stream of nitrogen. The reaction was monitored by taking <5 uL aliquots, diluting with 5–10 ml of methanol, and injecting the sample into the high pressure liquid chromatograph. Usually the disappearance of the starting materials was monitored. The mixture was worked-up as follows. It was poured into 150 ml of water. If a precipitate was present then it was filtered, washed, dried, weighed and recrystallized. If no solid precipitate was present, then the mixture was extracted with ether. The ether phase was dried over sodium sulfate and the solvent evaporated. Purification by chromatography on a silica column was utilized if more than one product was present in the mixture.

EXAMPLE 1

1-(4'-Methoxyphenyl)-4-phenyl-1,3-butadiene

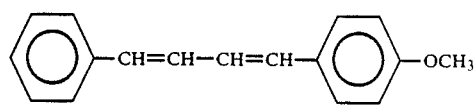

The reaction of anethole (1.48 g, 0.010 mol) and N-phenylbenzaldimine (1.81 g, 0.010 mol) in Na/DMF, 50 ml, at 90° C. for 4 hrs gave 1.20 g. (50%) of the title compound. The product recrystallized from ethanol has mp. 160°–162° C. (lit.[1] mp 163°–164° C.). UV (tetrahydrofuran) $\lambda_{max}$ (nm) (E): 340 (55200); FTIR (CDCl$_3$) v3082, 3062, 3029, 2960, 2936, 2912, 2839, 1603 (C=C), 1596 (C=C), 1575, 1512, 1508; $^1$H NMR (200 MHz, CDCl$_3$) delta (assignment): 3. (s, 3H, OCH3), 6.8 - (m, ),7. -7. (m, H, aromatic).

[1] C. C. Leznoff and R. J. Hayward Can. J. Chem. 48, 1842 (1970).

EXAMPLE 2

1,4-Diphenyl-1,3-butadiene

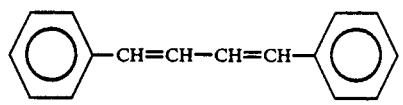

The reaction of trans-beta-methylstyrene (1.18 g, 0.010 mol) and N-phenylbenzaldimine (1.81 g, 0.010 mol) in Na/DMF (50 ml) for 2 hrs at 90° C. gave 1.12 g (54%) after column chromatography with petroleum ether/chloroform 4:1. Recrystallization from ethanol gave plates mp 150°–153° C. (lit.[1] 153° C. (23%)). FTIR (CDCl$_3$) V: 3083, 3063, 3028, 1612, 1595 (—C=C—), 1492, 1446; $^1$H NMR (200 MHz, CDCl$_3$) delta (assignment): 6.63–6.77 (tt, 2H, —C$_2$H—), 6.92–7.06 (tt, 2H, —C$_1$H—), 7.21–7.40 (m, 10H, aromatic); UV (tetrahydrofuran) $\lambda_{max}$ (nm) (E): 319 (46900), 330 (54800), 344 (35800).

[1]Vogel's op. cit. pp 804–805.

EXAMPLE 3

Bis{(4'-phenyl-1', 3'-butadienyl)-4-phenoxy}methane
Di(N-phenylcarboxaldimine-4-phenoxy) methane

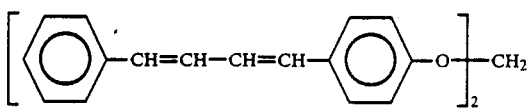

4-Hydroxybenzaldehyde (12.21 g, 0.100 mol) and potassium hydroxide (45.8% ; 12.25 g, 0.100 mol HO$^-$) were mixed in 50 ml of benzene and the theoretical amount of water was removed with a Dean-Stark trap. The benzene was evaporated off and dimethylformamide, 50 ml, containing dibromomethane (9.2 g, 0.053 mol) were added to the solid residue. The mixture was stirred for 2 hrs at 80° C. and di (4-carboxaldehyde-phenoxy)methane was precipitated by the addition of water (200 ml). A sample was purified mp 84°–85° C. from petroleum ether and characterized by infrared and $^1$H NMR. The reddish precipitate was dried. To this material was added aniline (2 eq) in benzene 50 ml and again the theoretical amount of water was removed. On cooling the benzene solution the dianil crystallized. This crop was suction-filtered and washed with a little more benzene. Recrystallization from benzene gave the above dianil (90% overall) mp 148°–151° C. Anal. calcd. for C$_{27}$H$_{22}$N$_2$O$_2$:C 79.78, H 5.46, N 6.89%; found: C 79.97, H 5.43, N 6.65%

Bis{(4'-phenyl-1',3'-butadienyl)-4-phenoxy}methane

Di(N-phenylcarboxaldimine-4-phenoxy)methane (4.06 g, 0.010 mol) and trans-beta-methylstyrene (2.36 g, 0.020 mol) in Na/DMF (50 ml) at 100° C. for 1 hr caused the mixture to cake. An additional 5 ml of DMF was added. Heating and stirring was continued for 3 hrs. The usual work-up of the precipitate afforded 4.40 g of brown-yellow powder. Recrystallization from chloroform, 800 ml, yielded 2.55 g (56%). Recrystallization from dimethylsulfoxide gave off-white plates mp 233°–235° C.

EXAMPLE 4

Bis{(4'-(4''-methoxyphenyl)-1',3'-butadienyl)-4-phenoxy}methane

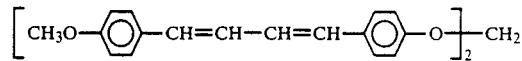

Di(N-phenylcarboxaldimine-4-phenoxy)methane (2.03 g, 0.0050 mol) and anethole (1.48 g, 0.010 mol) in Na/DMF, 50 ml, at 100° C. for 5 hrs gave after several washings of acetone and ethanol 1.4 g (54%) of the title compound as beige platelets. Recrystalization from dimethylsulfoxide gave colorless plates mp 246°–248° C. Anal. calcd. for C$_{35}$H$_{32}$O$_4$: C 81.37, H 6.24%; found: C 80.76, H 6.26%. MS [m/e (70 eV, % of base peak)] (CH$_3$O(C$_6$H$_4$)CH=CH—CH=CH(C$_6$H$_4$)O)CH$_2$)516 (M$^+$., 8.4), 515(M$^+$—H., 46.2), 251 (M$^+$—CH$_3$O(C$_6$H$_4$)CH=CH—CH =CH(C$_6$H$_4$)OCH$_2$., 57.7), 121 ( (CH$_3$O(C$_6$H$_4$)CH$_2$)$^+$, 100), 91((C$_6$H$_4$)CH$_2$$^+$., 78.6); HRMS (m/z) for C$_{35}$H$_{32}$O$_4$(M$^+$.), calcd. 516.230, found 516.241. UV (tetrahydrofuran) $\lambda_{max}$(nm) (E): 334 (105000), 346 (123000), 364 (95300). FTIR (KBr wafer) V: 3014, 2956, 2973, 2911, 2837, 1600 (C=C), 1505 cm$^{-1}$.

EXAMPLE 5

Bis{(4'-phenyl)-1',3'-butadienyl)-2-phenoxy}methane

Di-(2-propenylphenoxy) methane

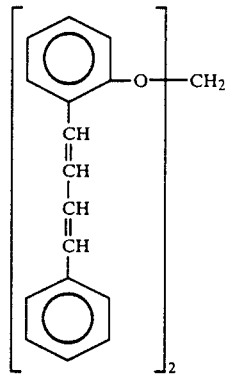

The preparation of 2-propenylphenol from phenol and allyl bromide is similar to that outlined[1]. The reaction of this compound with dibromomethane is similar to that described above for di (N-phenylcarboxaldimine-4-phenoxy)methane. The title compound was extracted with ether 3 × 100 ml portions from the aqueous dimethylformamide solution, washed with aqueous potassium hydroxide (10%) and then water. The ether phase was dried over sodium sulphate and the solvent was stripped off under reduced pressure. The oil which contained some (~5%) of a less polar component and at least two isomeric forms of the title compound, as indicated from high pressure liquid chromatography, was used without further purification in the reaction below.

[1]Vogel's "Textbook of practical organic chemistry" 4th ed. Wiley, New York. 1978. Chapt. IV. p752 and p754.

Di(N-phenylcarboxaldimine-2-phenoxy) methane

This compound was prepared in the same fashion as the 4-phenoxy analog above. The dialdehyde was recrystallized from ethanol, mp 133°–135° C., as white needles. The dianil recrystallized from ethanol as pale yellow needles, mp 86°-88° C. ¹H NMR (200 MHz, CDCl₃) delta (assignments): 5.92(s, 2H, OCH₂O), 7.09–7.40 (m, 16H, aromatic), 8.13 (s, 1H, aromatic), 8.18 (s, 1H, aromatic), 8.80 (s, 2H, PhNCH).

Bis{(4'-phenyl)-1',3'-butadienyl)-2-phenoxy}methane

Method A

Crude di(1'-propenyl-2-phenoxy)methane (2.80 g., 0.010 mol) and N-phenylbenzaldimine (3.62 g., 0.020 mol) in Na/DMF, 50 ml, at 100° C. for 1 hr gave 1.0 g. (22%) of the title compound. Recrystallization from benzene afforded colorless platelets mp 183°-184° C. Anal. Calcd. for C₃₃H₂₈O₂: C 86.81, H 6.18%; found: C 86.85, H 6.30%. ¹H NMR (20 MHz, CDCl₃) delta (assignment): 5.84 (s, 2H, OCH₂O), 6.58–6.62 (m, 2H, aromatic), 6.87–7.14(m, 8H, aromatic), 7.21–7.60 (m, 16H, aromatic. MS [m/e(70 eV, % of base peak)] ((C₆H₅—CH=CH—CH=CH(C₆H₄)O)₂—CH₂) 456 (M+., 12.2), 455 (M+—H., 23.4), 117 ((C₆H₅)CH=CH—CH₂)+., 100). FTIR (CDCl₃) V: 3082, 3064, 3027, 1595 (C=C), 1577, 1485, 1457, 1448, 1410 cm⁻¹. UV (tetrahydrofuran) λ$_{max}$ (nm) (E): 338 (85100).

Method B

Di(N-phenylcarboxaldimine-2-phenoxy)methane (2.03 g, 0.0050 mol) and trans-beta-methylstyrene (1.18 g, 0.010 mol) in Na/DMF 50 mL at 100° C. for 4 hrs gave the title compound identical with the product from method A above; yield 1.15 g (50%).

I claim:

1. A process for preparing an aromatic butadiene comprising:
   reacting an anil with an organic compound having a propenyl radical of formula —CH=CHCH₃ conjugated with an aromatic system.

2. A process according to claim 1, for preparing an aromatic alkene of formula (I):

$$R_1—CH=CH—X—R_2 \quad (I)$$

wherein R₁ and R₂, which may be the same or different, are selected from aryl and hetaryl radicals, and X is an ethylene radical —CH=CH— conjugated with the unsaturation of R₂, comprising reacting an anil of formula (II):

$$R_1—CH=NR_3 \quad (II)$$

in which R₁ is as defined above and R₃ is an aryl radical, with an organic compound of formula (III):

$$R_2—X—CH_3 \quad (III)$$

in which R₂ and X are as defined above.

3. A process according to claim 2, wherein R₃ is phenyl.

4. A process according to claim 3 wherein R₁ is unsubstituted or substituted phenyl.

5. A process according to claim 4 wherein R₂ is unsubstituted or substituted phenyl, provided that R₂ is not methyl substituted phenyl.

6. A process according to claim 1, for preparing an aromatic bis-butadiene of formula (XI):

$$R_2—X—CH=CH—R_4—Y—R_4—CH=CH—X—R_2 \quad (XI)$$

wherein R₂ is selected from aryl and hetaryl radicals, R₄ is selected from arylene and hetarylene radicals, X is an ethylene radical —CH=CH— conjugated with the unsaturation of R₂ and Y is a divalent bridging group comprising:
   reacting a dianil of formula (X):

$$R_3=N—CH—R_4—Y—R_4—CH=NR_3 \quad (X)$$

wherein R₃ is an aryl group and R₄ and Y are as defined above with an organic compound of formula (III)

$$R_2—X—CH_3 \quad (III)$$

in which R₂ and X are as defined above.

7. A process according to claim 6 wherein Y is selected from the group consisting of alkylene, arylene, heteroarylene, —OZO— and —SZS— wherein Z is alkylene, arylene or heteroarylene.

8. A process according to claim 1 wherein said reacting is carried out under strongly basic conditions.

9. A process according to claim 8 wherein said reacting is carried out in the presence of a base comprising an alkali metal amide.

10. A process according to claim 9 wherein said amide is generated in situ from sodium and dimethylformamide.

* * * * *